US012630420B2

(12) United States Patent
Park et al.

(10) Patent No.: US 12,630,420 B2
(45) Date of Patent: May 19, 2026

(54) HYDROGEN STORAGE MATERIALS COMPRISING NAPHTALENE GROUP AND THE METHOD FOR HYDROGEN STORAGE AND RELEASE USING THE SAME

(71) Applicant: KOREA RESEARCH INSTITUTE OF CHEMICAL TECHNOLOGY, Daejeon (KR)

(72) Inventors: Ji Hoon Park, Daejeon (KR); Kwan Yong Jeong, Daejeon (KR); Soo Min Kim, Daejeon (KR); Sunil Kwon, Daejeon (KR); Iljeong Heo, Daejeon (KR); Jin Hee Lee, Daejeon (KR); Tae Sun Chang, Daejeon (KR)

(73) Assignee: KOREA RESEARCH INSTITUTE OF CHEMICAL TECHNOLOGY, Daejeon (KR)

(*) Notice: Subject to any disclaimer, the term of this patent is extended or adjusted under 35 U.S.C. 154(b) by 1118 days.

(21) Appl. No.: 17/390,675

(22) Filed: Jul. 30, 2021

(65) Prior Publication Data

US 2022/0033258 A1 Feb. 3, 2022

(30) Foreign Application Priority Data

Aug. 3, 2020 (KR) ........................ 10-2020-0096898

(51) Int. Cl.

| | |
|---|---|
| ***C01B 3/0015*** | (2026.01) |
| ***C07C 15/24*** | (2006.01) |
| ***F17C 11/00*** | (2006.01) |

(52) U.S. Cl.

CPC ............ *C01B 3/0015* (2013.01); *C07C 15/24* (2013.01); *F17C 11/005* (2013.01); *F17C 2221/012* (2013.01)

(58) Field of Classification Search

CPC . C01B 3/0015; C01B 3/26; C01B 2203/1047; C01B 2203/1064;

(Continued)

(56) References Cited

U.S. PATENT DOCUMENTS 6,239,320 B1 * 5/2001 Mendoza ................. C09K 5/10
252/570
10,450,194 B2 * 10/2019 Boesmann ................ C01B 3/26

(Continued)

FOREIGN PATENT DOCUMENTS

CN 106542955 A 3/2017
JP S62-246997 A 10/1987

(Continued)

OTHER PUBLICATIONS

Preuster et al. (Liquid Organic Hydrogen Carriers (LOHCs): Toward a Hydrogen-free Hydrogen Economy, Accounts of Chemical Research, 2016). (Year: 2016).*

(Continued)

*Primary Examiner* — Anthony J Zimmer
*Assistant Examiner* — Logan Laclair
(74) *Attorney, Agent, or Firm* — Hauptman Ham, LLP

(57) ABSTRACT

Proposed are a naphthalene-based hydrogen storage material including a naphthalene group, the naphthalene-based hydrogen storage material being capable of being used as a hydrogen storage media for supplying hydrogen to a device using hydrogen such as a fuel cell and a hydrogen combustion device, and to a method of storing and releasing hydrogen using the same. The hydrogen storage material can exhibit a significantly high hydrogen capacity, and can have excellent cost competitiveness with the use of a low-cost organic compound which is commercially available in the art.

7 Claims, 2 Drawing Sheets

(58) Field of Classification Search
CPC .... C01B 2203/1614; C01B 2203/1628; C07C 15/24; C07C 15/27; C07C 5/02; C07C 5/367; F17C 11/005; F17C 2221/012; Y02E 60/32; Y02E 60/50; B01J 23/00; H01M 8/04216
See application file for complete search history.

(56) References Cited

U.S. PATENT DOCUMENTS

| | | | | |
|---|---|---|---|---|
| 2004/0223907 A1* | 11/2004 | Pez | ....................... | C01B 3/0015 423/658.2 |
| 2018/0093889 A1* | 4/2018 | Yoon | ....................... | B01J 23/44 |

FOREIGN PATENT DOCUMENTS

| | | |
|---|---|---|
| KR | 10-1990-0000877 B1 | 2/1990 |
| KR | 10-1845515 B1 | 4/2018 |
| KR | 10-1862012 B1 | 5/2018 |
| KR | 10-2019-0059462 A | 5/2019 |
| KR | 10-1987553 B1 | 6/2019 |

OTHER PUBLICATIONS

Korean Office Action issued on Jan. 21, 2022, for corresponding Korean Patent Application No. 10-2020-0096898; with English machine translation.
Extended European Search Report issued on Jan. 7, 2022, for corresponding European Patent Application No. 21188790.6.
Haiqing Guo et al., "Early Transition Metal-Catalyzed Cross-Coupling Reaction of Aryl Fluorides with a Phenethyl Grignard Reagent Accompanied by Rearrangement of the Phenethyl Group," Organometallics, 2006, vol. 25, pp. 2045-2048; cited in NPL No. 2.
Xu Shen et al., "One-pot reductive coupling reactions of acetyl naphthalene derivatives, tosylhydrazide, with arylboronic acids," Tetrahedron, 2017, vol. 73, pp. 785-793; cited in NPL No. 2.

* cited by examiner

HYDROGEN STORAGE MATERIALS COMPRISING NAPHTALENE GROUP AND THE METHOD FOR HYDROGEN STORAGE AND RELEASE USING THE SAME

CROSS REFERENCE TO RELATED APPLICATION

The present application claims priority to Korean Patent Application No. 10-2020-0096898, filed Aug. 3, 2020, the entire contents of which is incorporated herein for all purposes by this reference.

BACKGROUND OF THE INVENTION

Field of the Invention

The present disclosure relates to a naphthalene-based hydrogen storage material including a naphthalene group, the naphthalene-based hydrogen storage material being capable of being used as a hydrogen storage media for supplying hydrogen to a device using hydrogen, such as a fuel cell and a hydrogen combustion device, and to a method of storing and releasing hydrogen using the same.

Description of the Related Art

The depletion of fossil fuels and environmental pollution problems have led to a great demand for renewable alternative energy, and hydrogen is gaining attention as an alternative energy to fossil fuels. In particular, in the case of fuel cells and hydrogen combustion devices, hydrogen is used as an energy carrier. In order to apply the fuel cells and hydrogen combustion devices to, for example, automobiles and various electronic products, a technology for reliable and sustainable supply of hydrogen is required.

In a device that uses hydrogen, a system in which hydrogen is supplied from a separate hydrogen storage device (hydrogen supply device) whenever hydrogen is needed may be used. Representative examples thereof include compressed hydrogen storage and liquid hydrogen storage methods. These technologies may have issues with regard to cost and safety in transporting hydrogen from a hydrogen producer to a hydrogen consumer.

For example, hydrogen may be stored in compressed form in a high-pressure tank suitable for storage at maximum pressure of 875 bar. Also, hydrogen may be stored in low-temperature liquid form in a suitable cryogenic vessel, preferably in a superinsulated cryogenic vessel.

Meanwhile, as another way to store hydrogen, a system in which a material responsible for storing and generating hydrogen is provided in a device that uses hydrogen, and hydrogen is generated through the reaction of the material, may be used. Concerning this approach, for example, a method of using metal hydride, a method of using absorbents/carbon, a chemical hydrogen storage method, etc. have been proposed, and a hydrogen storage technology using various chemical hydrides such as ammonia borane, silane compounds, formic acid, etc. has been investigated.

Chemical hydrogen storage technology based on the above-mentioned compounds is in an experimental stage, and hydrogen is stored in an organic compound that is capable of being hydrogenated through a chemical reaction with hydrogen.

Specifically, a hydrogen-unloaded material A (hydrogen-lean form) is loaded with hydrogen to convert into a hydrogen-loaded material B (hydrogen-rich form), and this operation of hydrogen loading generally takes the form in the related art of a catalytic hydrogenation reaction under superatmospheric pressure. The hydrogen which is released from the hydrogen-loaded material B through a dehydrogenation reaction is usable as an energy source in a fuel cell or a combustion engine for example. The hydrogen-unloaded material A can be reloaded with hydrogen through a catalytic hydrogenation reaction under superatmospheric pressure. The hydrogen-loaded material B is beneficial to hydrogen storage and transport when it is liquid, and systems of this type are known as liquid organic hydrogen carriers (LOHCs).

These liquid organic hydrogen carriers (LOHCs) have the following advantages. First, LOHC has high hydrogen capacity per volume (>45 kg $H_2/m^3$, >1.5 $MWh/m^3$, based on material) and high hydrogen capacity per weight (>5.5 wt %, based on material). Second, LOHC can be repeatedly used to store and release hydrogen. Third, since LOHC is a liquid organic compound with similar material properties to gasoline, LOHC technology can be comparable with the existing fossil fuel-based storage and transport infrastructure without requiring large initial investment costs.

As one particularly known example of LOHC systems, a hydrogen storage and transport technology based on toluene has been developed by the Chiyoda Chemical Engineering & Construction Company in Japan. When hydrogen is reacted with toluene, toluene converts into liquid methylcyclohexane (MCH), which can be transported at ambient temperature and pressure. The methylcyclohexane compound has a hydrogen capacity of 6.1 wt %.

Another known example relates to using the material pair N-ethylcarbazole/perhydro-N-ethylcarbazole, which has a hydrogen capacity of about 5.8% by mass of hydrogen in a hydrogen storage and release system.

Examples of the related art concerning this are Korean Patent no. 10-1845515 (published on Apr. 4, 2018) that discloses a liquid hydrogen storage material containing 1,1'-biphenyl and 1, l'-methylenedibenzene in a weight ratio of 1:1.8 to 1:2.5, and Korean Patent No. 10-1862012 (published on Mar. 19, 2018) that discloses a hydrogen storage and release system using a pyridine-based hydrogen storage material. Another example is Korea Patent No. 10-1987553 (published on May 31, 2019), which discloses a liquid hydrogen storage material containing m-phenyltoluene (m=2, 3) for reversible dehydrogenation/hydrogenation reactions, or a binary eutectic mixture or a ternary eutectic mixture of m-phenyltoluene (m=2, 3, 4).

For large-scale commercial 1 use, a preferred liquid organic hydrogen carrier requires characteristics such as high hydrogen capacity per weight, suitable desorption temperature/pressure, excellent dynamic characteristics, and excellent reversibility, and organic compounds used as liquid organic hydrogen carriers also require low production costs.

Particularly in automobile applications, low hydrogen capacity per weight reduces gas mileage and distance traveled, so the development of a liquid organic hydrogen carrier having high hydrogen capacity is necessary.

The foregoing is intended merely to aid in the understanding of the background of the present disclosure, and is not intended to mean that the present disclosure falls within the purview of the related art that is already known to those skilled in the art.

Documents of Related Art (Patent Document 1) Korean Patent No. 10-1845515 (published on: Apr. 4, 2018)

(Patent Document 2) Korean Patent No. 10-1862012 (published on Mar. 19, 2018)

(Patent Document 3) Korean Patent No. 10-1987553 (published on May 31, 2019)

SUMMARY OF THE INVENTION

Accordingly, the present disclosure has been made keeping in mind the above problems occurring in the related art, and an objective of the present disclosure is to provide a novel naphthalene-based hydrogen storage material usable in an LOHC system, and to provide a system for storing and releasing hydrogen using the same.

In order to achieve the above objective, according to one aspect of the present disclosure, there is provided a hydrogen storage material including a naphthalene-based compound, wherein the naphthalene-based compound may be represented by the following Chemical Formula 1.

[Chemical Formula 1]

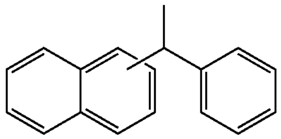

In an embodiment, the compound represented by Chemical Formula 1 may be formed by hydrogenation and dehydrogenation of a compound represented by the following Chemical Formula 5.

[Chemical Formula 5]

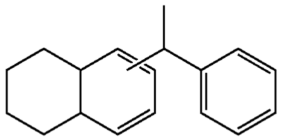

According to another aspect of the present disclosure, there is provided a method of storing and releasing hydrogen, the method including: 1) storing hydrogen in at least one of naphthalene-based compounds represented by the following Chemical Formula 1 through a hydrogenation reaction to form a hydrogenated compound represented by the following Chemical Formula 2; and 2) releasing hydrogen from the hydrogenated compound represented by Chemical Formula 2 through a hydrogenation reaction to form the compound represented by the following Chemical Formula 1.

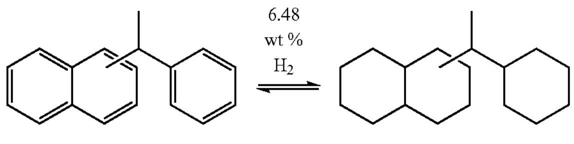

[Chemical Formula 1] [Chemical Formula 2]

In an embodiment, a hydrogenation catalyst used in step 1) may include at least one active material selected from the group consisting of Ru, Pt, Pd, Rh, and Ni.

In an embodiment, a dehydrogenation catalyst used in step 2) may include at least one active material selected from group VIIIB of the Periodic table of elements.

In an embodiment, the hydrogenation reaction in step 1) may be performed at a temperature of 110° C. to 230° C., and a pressure of 10 bar to 200 bar.

In an embodiment, the dehydrogenation reaction in step 2) may be performed at a temperature of 250° C. to 350° C., and a pressure of atmospheric pressure.

In an embodiment, a hydrogenation catalyst used in the hydrogenation reaction in step 1) may be included in an amount of 0.1 wt % to 70 wt % with respect to the amount of the hydrogen storage material.

In an embodiment, a dehydrogenation catalyst used in the dehydrogenation reaction in step 2) may be included in an amount of 0.1 wt % to 70 wt % with respect to the amount of the hydrogen storage material.

According to still another aspect of the present disclosure, there is provided a system for storing and releasing hydrogen, the system including a container in which the hydrogen storage material is stored.

The naphthalene-based hydrogen storage material according to the present disclosure has a structural feature in which a naphthalene ring and a benzene ring are connected to each other by $sp^3$ carbons, and can advantageously exhibit a high hydrogen capacity per unit weight compared to a conventional hydrogen storage material.

Furthermore, with the use of a low-cost organic compound which is commercially available in the art, the hydrogen storage material according to the present disclosure can have excellent cost competitiveness.

BRIEF DESCRIPTION OF THE DRAWINGS

The above and other objectives, features, and other advantages of the present disclosure will be more clearly understood from the following detailed description when taken in conjunction with the accompanying drawings, in which.

DETAILED DESCRIPTION OF THE INVENTION

Figure 1:
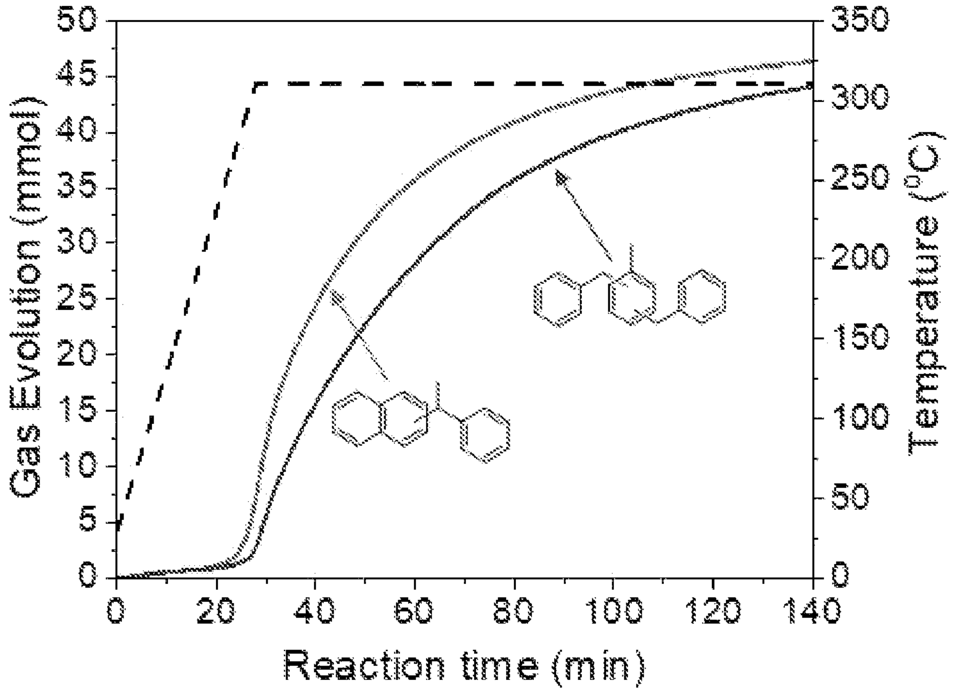
FIG. 1 is a graph illustrating a result of measuring the molecular number of hydrogen as a function of dehydrogenation reaction time during dehydrogenation of a compound resulting from complete hydrogenation of a naphthalene-based hydrogen storage material according to the present disclosure and a compound resulting from complete hydrogenation of dibenzyltoluene which is a commercially available heat transfer fluid acting as storage media.

Hereinbelow, exemplary embodiments of the present disclosure will be described in detail with reference to the accompanying drawings. Throughout the drawings, the same reference numerals will refer to the same or like parts.

Unless otherwise defined, all terms including technical and scientific terms used herein have the same meaning as commonly understood by one of ordinary skill in the art to which the present disclosure belongs. Generally, the nomenclature used herein and the experiment methods, which will be described below, are those well known and commonly employed in the art.

It will be further understood that the terms "comprise", "include", "have", etc. when used in this specification, specify the presence of stated features, integers, steps, operations, elements, components, and/or combinations of them but do not preclude the presence or addition of one or more other features, integers, steps, operations, elements, components, and/or combinations thereof.

The term "liquid" as used herein refers to a liquid state.

The term "hydrogen storage material" as used herein refers to a material which reacts with a material including a hydrogen (H) atom to store the hydrogen (H) atom through a chemical bond, and reversibly releases hydrogen ($H_2$) under a predetermined condition.

In an aspect, the present disclosure provides a hydrogen storage material including a naphthalene-based compound that can be used as a hydrogen storage material for supplying hydrogen to devices using hydrogen such as fuel cells and hydrogen combustion devices. The naphthalene-based compound is represented by the following Chemical Formula 1.

[Chemical Formula 1]

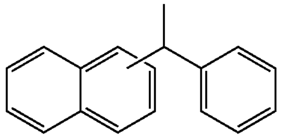

The naphthalene-based hydrogen storage material according to the present disclosure has a structural feature in which a branched hydrocarbon linking group with $sp^3$ carbons is connected to a naphthalene structure, and a benzene structure that can contribute to hydrogen capacity is bound to the above linking group. A naphthalene ring and a benzene ring each have a non-condensed conjugated aromatic unit. Examples of the naphthalene-based hydrogen storage material according to the present disclosure include 1-(1-phenylethyl) naphthalene represented by the following Chemical Formula 3 and 2-(1-phenylethyl) naphthalene represented by the following Chemical Formula 4, which may be used alone or in combination with each other.

[Chemical Formula 3]

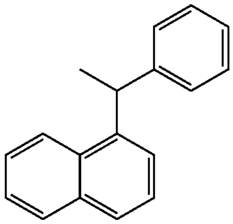

[Chemical Formula 4]

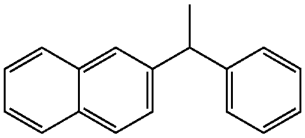

The naphthalene-based compound represented by Chemical Formula 1 contains both a naphthalene structure and a benzene structure that contribute to dehydrogenation/hydrogenation reactions in the molecular structure thereof, thereby exhibiting a high hydrogen capacity of about 6.48 wt % by mass of hydrogen in a hydrogen storage and release system.

The naphthalene-based hydrogen storage material represented by Chemical Formula 1 is liquid at room temperature due to having a lower melting point than room temperature. Therefore, it can not only be prepared in a liquid state at room temperature and pressure without the use of a separate solvent or additive, but also can exhibit low viscosity, which is beneficial to transport using a pipe.

Accordingly, the hydrogen storage material according to the present disclosure can exhibit a much higher hydrogen capacity per weight and volume than that of compressed gas, and can be facile to store and transport in a liquid state. Therefore, the use of the hydrogen storage material according to the present disclosure enables cost-effective storage and transport of hydrogen without requiring unnecessary initial investment costs.

Furthermore, the naphthalene-based hydrogen storage material represented by Chemical Formula 1 can exhibit high stability in the dehydrogenation reaction due to high boiling point thereof.

The naphthalene-based compound represented by Chemical Formula 1 according to the present disclosure may be prepared through hydrogenation and dehydrogenation of 1-phenyl-1-tetrahydronaphthylethane (PTE) represented by Chemical Formula 5 below. In this case, 1-phenyl-1-tetrahydronaphthylethane (PTE) may be 1,2,3,4-tetrahydro-5-(1-phenylethyl) naphthalene represented by Chemical Formula 6 or 1,2,3,4-tetrahydro-6-(1-phenylethyl) naphthalene represented by Chemical Formula 7, or an isomer mixture thereof.

[Chemical Formula 5]

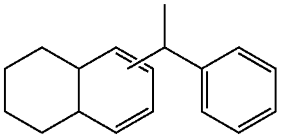

[Chemical Formula 6]

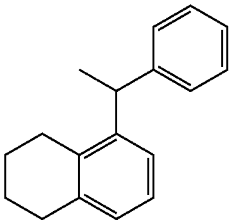

[Chemical Formula 7]

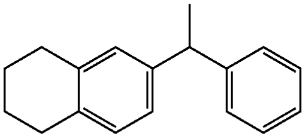

1-phenyl-1-tetrahydronaphthylethane (PTE) represented by Chemical Formula 5 may be one commercially available from The Dow Chemical Company as Dowtherm™ RP heat transfer fluid. The hydrogen storage material herein may be synthesized through hydrogenation/dehydrogenation reactions of PTE. Therefore, with the use of a low-cost organic compound which is commercially available in the art, the hydrogen storage material according to the present disclosure can have excellent cost competitiveness.

Although the possibility of hydrogen loading 1-phenyl-1-tetrahydronaphthylethane (PTE) has hitherto not been considered anywhere, the present inventors have found that PTE is capable of conversion into a hydrogen-rich form as a hydrogen carrier and of efficient release of hydrogen.

Furthermore, since the hydrogen storage material is used as storage media for hydrogen, it is advantageous to release hydrogen as rapidly as possible. In view of this, the hydrogen storage material according to the present disclosure is expected to be very useful as a hydrogen storage material by exhibiting rapid hydrogen release characteristics.

In another aspect, the present disclosure provides a method of storing and releasing hydrogen. The method includes the steps of: 1) storing hydrogen in a naphthalene-based hydrogen storage material represented by the following Chemical Formula 1 through a hydrogenation reaction;

and 2) releasing hydrogen from the hydrogenated naphthalene-based hydrogen storage material through a dehydrogenation reaction. The naphthalene-based hydrogen storage material represented by Chemical Formula 1 may undergo reversible hydrogenation/dehydrogenation reactions as illustrated in Chemical Reaction Formula 1.

Chemical Reaction Formula 1

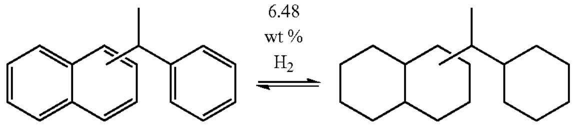

[Chemical Formula 1] [Chemical Formula 2]

Hereinafter, the method of storing and releasing hydrogen using the naphthalene-based hydrogen storage material according to the present disclosure will be described in more detail.

The naphthalene-based hydrogen storage material according to the present disclosure is characterized by binding and releasing hydrogen upon contact with a metal-containing catalyst in a reactor. Here, the metal-containing catalyst used for hydrogen loading/unloading may be a supported catalyst containing metal particles finely dispersed on a porous support. The porous support may be a support including a material used in the field of catalyst preparation, but is not particularly limited thereto. Specifically, the support may include a porous material such as activated carbon (C), alumina, silica, zeolite, etc.

The metal-containing catalyst may include an active constituent in an amount ranging from 0.1 wt % to 15 wt % with respect to the total weight of the catalyst, preferably 0.5 wt % to 10 wt %, and more preferably in terms of catalytic activity, 0.5 wt % to 5 wt %. When the amount of the active constituent is less than 0.1 wt %, active sites that determine catalytic activity per unit area of the catalyst do not appear sufficiently. On the other hand, the amount thereof exceeds 15 wt %, the increase in the number of the active sites with the increase in the amount of the active constituent is insignificant. Therefore, increasing the amount of the supported active constituent is not cost effective.

Specifically, in the hydrogenation reaction in step 1), a hydrogenation catalyst may be used to accelerate the hydrogenation reaction. The catalyst may include at least one active metal selected from the group consisting of Ru, Pt, Pd, Rh, and Ni, and alumina may be used as a support for the active metal. Specifically, the hydrogenation catalyst may include, but is not limited to, at least one selected from the group consisting of $Ru/Al_2O_3$, $Pt/Al_2O_3$, $Pd/Al_2O_3$, $Ni/Al_2O_3$, Ru—$Pt/Al_2O_3$, Ru—$Pd/Al_2O_3$, and Pt—$Pd/Al_2O_3$.

In addition, in the hydrogenation reaction in step 1), the amount of the hydrogenation catalyst introduced into the reactor is preferably 0.1 wt % to 70 wt % with respect to the amount of the hydrogen storage material. When the amount of the hydrogenation catalyst is less than 0.1 wt %, a sufficient catalytic activity effect is not exhibited. On the other hand, when the amount thereof exceeds 70 wt %, this is not cost effective in terms of the effect of increasing the catalytic activity effect with the catalyst amount. In this case, the amount of the hydrogenation catalyst is calculated as the total amount of the supported catalyst including the active metal and the support for the active metal.

Furthermore, the hydrogenation reaction in step 1) may be performed at a temperature of 110° C. to 230° C., and a pressure of 10 bar to 200 bar. When the temperature of the hydrogenation reaction is less than 110° C. or the pressure thereof is less than 10 bar, the rate of the hydrogenation reaction may be lowered. On the other hand, when the temperature thereof exceeds 230° C., there is a possibility of thermal decomposition of the hydrogen storage material.

In the dehydrogenation reaction in step 2), a dehydrogenation catalyst may be used to accelerate the dehydrogenation reaction. In this case, the catalyst may include, but is not limited to, at least one metal selected from group VIIIB of the Periodic table of elements.

In addition, in the dehydrogenation reaction in step 2), the amount of the dehydrogenation catalyst introduced into the reactor is preferably 0.1 wt % to 70 wt % with respect to the amount of the hydrogen storage material.

When the amount of the dehydrogenation catalyst is less than 0.1 wt %, a sufficient catalytic activity effect is not exhibited. On the other hand, when the amount thereof exceeds 70 wt %, this is not cost effective in terms of in the effect of increasing the catalytic activity effect with the catalyst amount.

In this case, the amount of the dehydrogenation catalyst is calculated as the total amount of the supported catalyst including the active metal and the support for the active metal.

The dehydrogenation reaction in step 2) may be performed at a temperature of 250° C. to 350° C., and a pressure of atmospheric pressure to 3 bar.

In another aspect, the present disclosure provides a system for storing and releasing hydrogen. The system includes a container in which the hydrogen storage material represented by Chemical Formula 1 is stored. The hydrogen storage material represented by Chemical Formula 1 may be produced through hydrogenation and dehydrogenation reactions of 1-phenyl-1-tetrahydronaphthylethane (PTE) represented by Chemical Formula 5.

Hereinafter, Examples and Comparative Examples of the method and system for storing and releasing hydrogen using the naphthalene-based hydrogen storage material according to the present disclosure will be described in detail with reference to accompanying drawings.

Specific structural and functional descriptions of embodiments of the present disclosure disclosed herein are only for illustrative purposes of the preferred embodiments of the present disclosure, not intended to limit the scope of the present disclosure. Therefore, it should be understood that other equivalents and modifications may be included within the spirit and scope of the present disclosure as defined by the appended claims.

Hydrogen storage material according to the present disclosure 1: Compound represented by Chemical Formula 1

A hydrogen storage material may be produced through reversible de/hydrogenation reactions using commercially available Dowtherm™ RP. The Dowtherm™ RP was purchased from the Samyang Oil Company and used as received. The Dowtherm™ RP was hydrogenated at 180° C. in the presence of 5 wt % $Ru/Al_2O_3$ (in an amount 0.6 mol % with respect to the Dowtherm™ RP) and then dehydrogenated at 290° C. in the presence of 1 wt % Pt/C to obtain a compound represented by Chemical Formula 1.

Comparative Hydrogen Storage Material: MSH (Marlotherm™ SH, Dibenzyltoluene)

As a comparative hydrogen storage material, Marlotherm™ SH, dibenzyltoluene used as a commercially available hydrogen storage material, was purchased from the Sasol Company and used as received.

Examples and Comparative Examples

Hydrogenation Reaction

A hydrogenation reaction was carried out in a Parr 4598 reactor. 50 mmol of each $H_2$-lean LOHC reactant illustrated in Table 1 below and 0.8 mol % of 5 wt % $Ru/Al_2O_3$ as a commercially available catalyst were added. After purging the reactor with Ar gas 5 times, the temperature in the reactor was raised to 180° C. When the temperature reached 180° C., $H_2$ was added under a desired pressure. The pressure was maintained with a back pressure regulator. While maintaining stirring (1 ratio rpm), the hydrogenation reaction was carried out for a sufficient period of time until it was terminated. After the hydrogenation was terminated, the temperature in the reactor was lowered to room temperature. The amount of $H_2$ consumed was calculated using the pressure consumed in a burette, each $H_2$-rich LOHC reactant was analyzed by FID detector GC (Agilent 6280N) and NMR, and the results are illustrated in Table 1 below.

TABLE 1

| Classification | Hydrogenation reactant | Hydrogenation reaction time (hr) | Hydrogenation reaction pressure (bar) | Hydrogenation yield compared to theory (%) |
|---|---|---|---|---|
| Example 1 | Dowtherm ™ | 2 | 50 | 99 |
| Example 2 | Phenylethylnaphthalene | 2 | 50 | 99 |
| Example 3 | Dowtherm ™ | 2 | 35 | 99 |
| Comparative Example 1 | Dibenzyltoluene (Marlotherm ™ SH) | 2 | 50 | 99 |

From Table 1 above, it can be confirmed that in the case of the hydrogenation carried out in the presence of the Ru catalyst, complete hydrogenation was achieved by an amount corresponding to a final theoretical capacity of each storage media. It can be also confirmed that phenylethylnaphthalene represented by Chemical Formula 1 could be completely hydrogenated under the same conditions compared to partially hydrogenated Dowtherm™ RP represented by Chemical Formula 5. In this case, complete hydrogenation was possible even when the pressure was lowered to 35 bar. In addition, similar hydrogenation performance was confirmed compared to dibenzyltoluene, which is a commercially available heat transfer fluid acting as storage media.

Dehydrogenation Reaction

A hydride resulting from the hydrogenation reaction was subjected to a dehydrogenation reaction. The dehydrogenation reaction was carried out under the conditions illustrated in Table 2 below in the presence of 1 wt % Pt/C.

As dehydrogenation reactants, $H_2$-rich LOHC reactants as illustrated in Table 2 below were used. Each of the $H_2$-rich LOHC reactants was dehydrogenated in a two-neck Schlenk flask. After purging the flask with Ar gas for 5 minutes to remove moisture and oxygen therein, the temperature in the flask was raised to a dehydrogenation reaction temperature (290° C. or 310° C.) at a rate of 10° C./min, and then the dehydrogenation reaction was carried out for 2 hours while maintaining stirring. The volume of generated $H_2$ gas was measured using the amount of oil displaced from a burette, and the conversion rate, selectivity, and dehydrogenation yield were calculated using the values of GC measurement results. The measurement results are illustrated in Table 2 below.

TABLE 2

| Classification | Dehydrogenation reactant | Reaction temperature (° C.) | Catalyst amount (mol %) | Hydrogenation yield compared to theory (%) |
|---|---|---|---|---|
| Example 3 | Perhydro-phenylethyl naphthalene | 310 | 0.6 | 99 |
| Example 4 | Perhydro-phenylethyl naphthalene | 290 | 0.6 | 56 |
| Example 5 | Perhydro-phenylethyl naphthalene | 290 | 0.8 | 81 |
| Example 6 | Perhydro-phenylethyl naphthalene | 290 | 1 | 96 |
| Comparative Example 3 | Perhydro-dibenzyltoluene | 310 | 0.6 | 96 |

FIG. 1 illustrates a result of subjecting commercially purchased Dowtherm™ RP to hydrogenation and dehydrogenation, followed by hydrogenation again.

As can be confirmed from Table 2 above, a storage media represented by Chemical Formula 2, which resulted from the hydrogenation of a reactant represented by Chemical Formula 1, underwent an efficient dehydrogenation reaction under the condition of 290° C. or 310° C. In particular, under the condition of 310° C., a high dehydrogenation yield of 99% was exhibited, and even under the condition of 290° C., a dehydrogenation yield of 96% was exhibited through the increase in the catalyst amount. In Comparative Example 3, a storage media that resulted from the hydrogenation of Marlotherm™ SH, which is a commercially available heat transfer fluid, acting as storage media also exhibited a high dehydrogenation yield at 310° C. However, due to a relatively low theoretical capacity thereof, there was a difference in the amount of hydrogen released, and the results are illustrated in FIG. 1.

Figure 2:
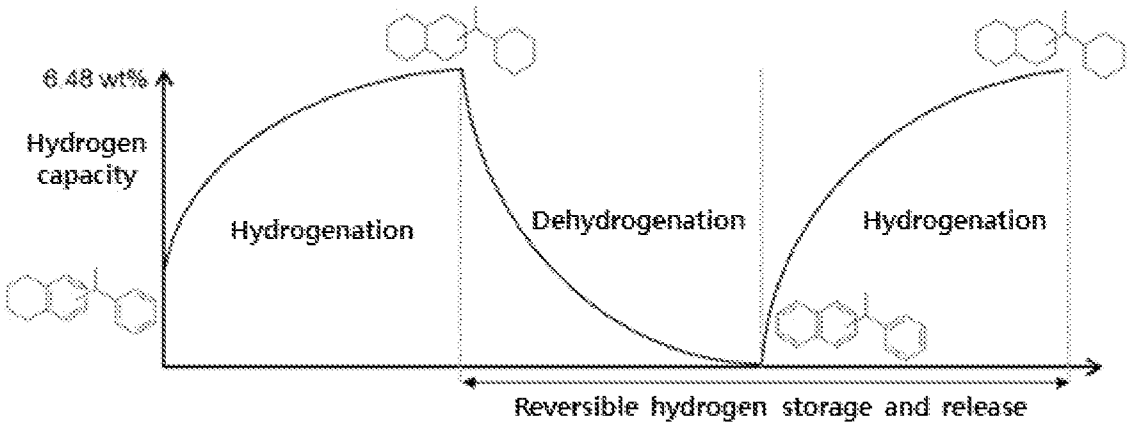
FIG. 2 is a graph illustrating the hydrogen capacity of the naphthalene-based hydrogen storage material according to the present disclosure using 1-phenyl-1-tetrahydronaphthylethane (PTE) as a starting material, in which the hydrogen capacity varies with reversible hydrogen storage and release.

FIG. 2 illustrates a result of using commercially available 1-phenyl-1-tetrahydronaphthylethane (Dowtherm™ RP) heat transfer fluid represented by Chemical Formula 5 as a starting material for the above hydrogenation and dehydrogenation reactions and repeatedly subjecting the 1-phenyl-1-tetrahydronaphthylethane to hydrogenation and dehydrogenation reactions. It can be confirmed from FIG. 2 that the Dowtherm™ RP was converted into a naphthalene-based hydrogen storage material according to the present disclosure after the hydrogenation, and could be used repeatedly. Therefore, this indicates that even a commercially available heat transfer fluid of relatively low cost could be excellently used as a starting material for the production of a hydrogen storage media, which is the objective of the present disclosure.

Although the preferred embodiments of the present disclosure have been disclosed for illustrative purposes, those skilled in the art will appreciate that various modifications, additions, and substitutions are possible, without departing from the scope and spirit of the disclosure. Therefore, the scope of the present disclosure should be defined by the appended claims and equivalents thereof.

What is claimed is:

1. A method of storing and releasing hydrogen, the method comprising:

1) Storing hydrogen in a liquid hydrogen storage material consisting of a naphthalene-based material, which is liquid at room temperature and pressure, and which is a compound represented by the following Chemical Formula 1, by hydrogenating the compound represented by Chemical Formula 1 to form a hydrogenated compound represented by the following Chemical Formula 2; and 2) Releasing hydrogen from the liquid hydrogen storage material by dehydrogenating the hydrogenated compound represented by Chemical Formula 2 to form the compound represented by Chemical Formula 1

[Chemical Formula 1]

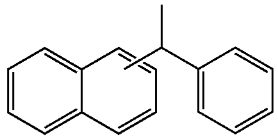

[Chemical Formula 2]

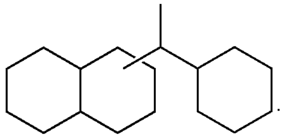

2. The method of claim 1, wherein a hydrogenation catalyst used in step 1) comprises at least one metal selected from the group consisting of Ru, Pt, Pd, Rh, and Ni as an active material.

3. The method of claim 1, wherein a dehydrogenation catalyst used in step 2) comprises at least one metal selected from group VIIIB of the Periodic table of elements as an active material.

4. The method of claim 1, wherein the hydrogenation reaction in step 1) is performed at a temperature of 110° C. to 230° C., and a pressure of 10 bar to 200 bar.

5. The method of claim 1, wherein the dehydrogenation reaction in step 2) is performed at a temperature of 250° C. to 350° C., and a pressure of atmospheric pressure.

6. The method of claim 1, wherein a hydrogenation catalyst used in the hydrogenation reaction in step 1) is included in an amount of 0.1 wt % to 70 wt % with respect to an amount of the hydrogen storage material.

7. The method of claim 1, wherein a dehydrogenation catalyst used in the dehydrogenation reaction in step 2) is included in an amount of 0.1 wt % to 70 wt % with respect to an amount of the hydrogen storage material.

* * * * *